US010905411B2

(12) United States Patent
Racenet et al.

(10) Patent No.: US 10,905,411 B2
(45) Date of Patent: Feb. 2, 2021

(54) SURGICAL SUTURING AND GRASPING DEVICE

(71) Applicant: Covidien LP, Mansfield, MA (US)

(72) Inventors: Danyel J. Racenet, Killingworth, CT (US); Kevin S. Sniffin, Roxbury, CT (US)

(73) Assignee: COVIDIEN LP, Mansfield, MA (US)

( * ) Notice: Subject to any disclaimer, the term of this patent is extended or adjusted under 35 U.S.C. 154(b) by 194 days.

(21) Appl. No.: 16/126,217

(22) Filed: Sep. 10, 2018

(65) Prior Publication Data

US 2019/0133571 A1 May 9, 2019

Related U.S. Application Data

(60) Provisional application No. 62/581,160, filed on Nov. 3, 2017.

(51) Int. Cl.
*A61B 17/04* (2006.01)
*A61B 34/35* (2016.01)
*A61B 17/062* (2006.01)
*A61B 17/29* (2006.01)
(Continued)

(52) U.S. Cl.
CPC ........ *A61B 17/0469* (2013.01); *A61B 17/062* (2013.01); *A61B 17/29* (2013.01); *A61B 34/35* (2016.02); *A61B 34/30* (2016.02); *A61B 2017/00353* (2013.01); *A61B 2017/00367* (2013.01); *A61B 2017/00477* (2013.01); *A61B 2017/2936* (2013.01)

(58) Field of Classification Search
CPC ... A61B 34/35; A61B 17/062; A61B 17/0469; A61B 17/29; A61B 2017/00367; A61B 2017/2936; A61B 2017/00353; A61B 2017/2938; A61B 34/30; A61B 2017/00477; A61B 2017/2926
See application file for complete search history.

(56) References Cited

U.S. PATENT DOCUMENTS

| 848,126 | A | * | 3/1907 | Roosevelt | ............ | A61B 17/122 |
| | | | | | | 606/157 |
| 1,037,864 | A | | 9/1912 | Carlson et al. | | |
| 1,131,163 | A | | 3/1915 | Saunders et al. | | |

(Continued)

FOREIGN PATENT DOCUMENTS

EP 0647431 A2 4/1995
EP 1261286 B1 10/2009
(Continued)

OTHER PUBLICATIONS

International Search Report dated Feb. 25, 2019, issued in PCT/US2018/058095.

*Primary Examiner* — Phong Son H Dang
(74) *Attorney, Agent, or Firm* — Carter, DeLuca & Farrell LLP

(57) ABSTRACT

An end effector for a suturing and grasping device includes a stationary jaw member, a suturing jaw member, and a grasping jaw member. The suturing jaw member is selectively movable relative to the stationary jaw member to drive a suturing needle between the suturing jaw member and the stationary jaw member. The grasping jaw member is selectively movable relative to the stationary jaw member to grasp tissue between the stationary jaw member and the grasping jaw member.

8 Claims, 8 Drawing Sheets

(51) Int. Cl.
    *A61B 17/00*    (2006.01)
    *A61B 34/30*    (2016.01)

(56)            References Cited

U.S. PATENT DOCUMENTS

| | | | |
|---|---|---|---|
| 1,293,565 A | 2/1919 | Smit | |
| 1,449,087 A | 3/1923 | Bugbee | |
| 1,513,367 A * | 10/1924 | Brix | A61B 17/02 |
| | | | 606/157 |
| 1,822,330 A | 9/1931 | Ainslie | |
| 1,876,792 A | 9/1932 | Thompson | |
| 2,213,830 A | 9/1940 | Anastasi | |
| 2,214,985 A * | 9/1940 | Bachmann | A61B 17/2812 |
| | | | 81/303 |
| 2,327,353 A | 8/1943 | Karle | |
| 2,880,728 A | 4/1959 | Rights | |
| 3,073,311 A | 1/1963 | Tibbs et al. | |
| 3,090,386 A | 5/1963 | Curtis | |
| 3,349,772 A | 10/1967 | Rygg | |
| 3,470,875 A | 10/1969 | Johnson | |
| 3,807,407 A | 4/1974 | Schweizer | |
| 3,842,840 A | 10/1974 | Schweizer | |
| 3,901,244 A | 8/1975 | Schweizer | |
| 3,946,740 A | 3/1976 | Bassett | |
| 4,021,896 A | 5/1977 | Stierlein | |
| 4,109,658 A | 8/1978 | Hughes | |
| 4,161,951 A | 7/1979 | Scanlan, Jr. | |
| 4,164,225 A | 8/1979 | Johnson et al. | |
| 4,236,470 A | 12/1980 | Stenson | |
| 4,345,601 A | 8/1982 | Fukuda | |
| 4,373,530 A | 2/1983 | Kilejian | |
| 4,452,246 A * | 6/1984 | Bader | A61B 17/0467 |
| | | | 30/131 |
| 4,471,781 A | 9/1984 | Di Giovanni et al. | |
| 4,491,135 A | 1/1985 | Klein | |
| 4,580,567 A | 4/1986 | Schweitzer et al. | |
| 4,621,640 A | 11/1986 | Mulhollan et al. | |
| 4,635,638 A | 1/1987 | Weintraub et al. | |
| 4,890,615 A | 1/1990 | Caspari et al. | |
| 4,923,461 A | 5/1990 | Caspari et al. | |
| 4,935,027 A | 6/1990 | Yoon | |
| 4,957,498 A | 9/1990 | Caspari et al. | |
| 5,037,433 A | 8/1991 | Wilk et al. | |
| 5,042,707 A | 8/1991 | Taheri | |
| 5,059,201 A | 10/1991 | Asnis | |
| 5,100,421 A | 3/1992 | Christoudias | |
| 5,100,430 A | 3/1992 | Avellanet et al. | |
| 5,171,257 A | 12/1992 | Ferzli | |
| 5,181,919 A | 1/1993 | Bergman et al. | |
| 5,207,693 A | 5/1993 | Phillips | |
| 5,209,747 A | 5/1993 | Knoepfler | |
| 5,217,471 A | 6/1993 | Burkhart | |
| 5,242,458 A | 9/1993 | Bendel et al. | |
| 5,254,126 A | 10/1993 | Filipi et al. | |
| 5,261,917 A * | 11/1993 | Hasson | A61B 17/0469 |
| | | | 606/139 |
| 5,281,220 A | 1/1994 | Blake, III | |
| 5,300,082 A | 4/1994 | Sharpe et al. | |
| 5,308,353 A | 5/1994 | Beurrier | |
| 5,314,445 A | 5/1994 | Heidmueller et al. | |
| 5,330,502 A | 7/1994 | Hassler et al. | |
| 5,336,230 A | 8/1994 | Leichtling et al. | |
| 5,350,391 A | 9/1994 | Iacovelli | |
| 5,374,277 A | 12/1994 | Hassler | |
| 5,389,103 A | 2/1995 | Melzer et al. | |
| 5,403,342 A | 4/1995 | Tovey et al. | |
| 5,439,478 A | 8/1995 | Palmer | |
| 5,441,494 A * | 8/1995 | Ortiz | B25J 3/00 |
| | | | 294/213 |
| 5,454,823 A | 10/1995 | Richardson et al. | |
| 5,454,827 A | 10/1995 | Aust et al. | |
| 5,456,695 A * | 10/1995 | Herve Dallemagne | |
| | | | A61B 17/0218 |
| | | | 606/198 |
| 5,480,406 A | 1/1996 | Nolan et al. | |
| 5,540,706 A | 7/1996 | Aust et al. | |
| 5,564,615 A | 10/1996 | Bishop et al. | |
| 5,575,799 A | 11/1996 | Bolanos et al. | |
| 5,582,617 A | 12/1996 | Klieman et al. | |
| 5,591,181 A | 1/1997 | Stone et al. | |
| 5,601,224 A | 2/1997 | Bishop et al. | |
| 5,620,415 A | 4/1997 | Lucey et al. | |
| 5,643,294 A | 7/1997 | Tovey et al. | |
| 5,674,229 A | 10/1997 | Tovey et al. | |
| 5,690,652 A | 11/1997 | Wurster et al. | |
| 5,690,653 A | 11/1997 | Richardson et al. | |
| 5,735,849 A | 4/1998 | Baden et al. | |
| 5,752,973 A | 5/1998 | Kieturakis | |
| 5,759,188 A | 6/1998 | Yoon | |
| 5,766,196 A | 6/1998 | Griffiths | |
| 5,776,075 A * | 7/1998 | Palmer | A61B 10/06 |
| | | | 600/564 |
| 5,779,646 A | 7/1998 | Koblish et al. | |
| 5,792,165 A | 8/1998 | Klieman et al. | |
| 5,797,537 A | 8/1998 | Oberlin et al. | |
| 5,797,927 A | 8/1998 | Yoon | |
| 5,814,054 A | 9/1998 | Kortenbach et al. | |
| 5,817,119 A | 10/1998 | Klieman et al. | |
| 5,827,323 A | 10/1998 | Klieman et al. | |
| 5,865,836 A | 2/1999 | Miller | |
| 5,871,490 A | 2/1999 | Schulze et al. | |
| 5,876,412 A | 3/1999 | Piraka | |
| 5,897,563 A | 4/1999 | Yoon et al. | |
| 5,906,630 A | 5/1999 | Anderhub et al. | |
| 5,908,428 A | 6/1999 | Scirica et al. | |
| 5,925,064 A * | 7/1999 | Meyers | A61B 17/062 |
| | | | 606/205 |
| 5,928,136 A | 7/1999 | Barry | |
| 5,954,731 A | 9/1999 | Yoon | |
| 5,954,733 A | 9/1999 | Yoon | |
| 5,957,937 A | 9/1999 | Yoon | |
| 5,980,538 A | 11/1999 | Fuchs et al. | |
| 5,984,932 A | 11/1999 | Yoon | |
| 5,993,466 A | 11/1999 | Yoon | |
| 5,993,467 A | 11/1999 | Yoon | |
| 5,997,565 A | 12/1999 | Inoue | |
| 6,004,332 A | 12/1999 | Yoon et al. | |
| 6,017,358 A | 1/2000 | Yoon et al. | |
| 6,027,522 A | 2/2000 | Palmer | |
| 6,077,277 A * | 6/2000 | Mollenauer | A61B 17/04 |
| | | | 606/139 |
| 6,077,287 A | 6/2000 | Taylor et al. | |
| 6,080,180 A | 6/2000 | Yoon et al. | |
| 6,086,601 A | 7/2000 | Yoon | |
| 6,126,665 A | 10/2000 | Yoon | |
| 6,139,563 A | 10/2000 | Cosgrove, III et al. | |
| 6,143,005 A | 11/2000 | Yoon et al. | |
| 6,171,316 B1 | 1/2001 | Kovac et al. | |
| 6,206,893 B1 | 3/2001 | Klein et al. | |
| 6,214,028 B1 | 4/2001 | Yoon et al. | |
| 6,223,100 B1 | 4/2001 | Green | |
| 6,224,614 B1 | 5/2001 | Yoon | |
| 6,261,307 B1 | 7/2001 | Yoon et al. | |
| 6,299,625 B1 * | 10/2001 | Bacher | A61B 17/2909 |
| | | | 606/167 |
| 6,319,262 B1 | 11/2001 | Bates et al. | |
| 6,358,259 B1 | 3/2002 | Swain et al. | |
| 6,494,888 B1 | 12/2002 | Laufer et al. | |
| 6,506,196 B1 | 1/2003 | Laufer | |
| 6,517,539 B1 | 2/2003 | Smith et al. | |
| 6,569,105 B1 | 5/2003 | Kortenbach et al. | |
| 6,582,450 B2 | 6/2003 | Ouchi | |
| 6,638,287 B2 | 10/2003 | Danitz et al. | |
| 6,663,639 B1 | 12/2003 | Laufer et al. | |
| 6,663,641 B1 | 12/2003 | Kovac et al. | |
| 6,666,854 B1 | 12/2003 | Lange | |
| 6,676,676 B2 | 1/2004 | Danitz et al. | |
| 6,743,239 B1 | 6/2004 | Kuehn et al. | |
| 6,743,240 B2 | 6/2004 | Smith et al. | |
| 6,755,843 B2 | 6/2004 | Chung et al. | |
| 6,773,441 B1 | 8/2004 | Laufer et al. | |
| 6,821,285 B2 | 11/2004 | Laufer et al. | |
| 6,835,200 B2 | 12/2004 | Laufer et al. | |
| 6,889,116 B2 | 5/2005 | Jinno | |

(56) References Cited

U.S. PATENT DOCUMENTS

| | | |
|---|---|---|
| 6,936,061 B2 | 8/2005 | Sasaki |
| 6,972,017 B2 | 12/2005 | Smith et al. |
| 6,981,628 B2 | 1/2006 | Wales |
| 6,997,931 B2 | 2/2006 | Sauer et al. |
| 7,052,489 B2 | 5/2006 | Griego et al. |
| RE39,152 E | 6/2006 | Aust et al. |
| 7,063,715 B2 | 6/2006 | Onuki et al. |
| 7,107,124 B2 | 9/2006 | Green |
| 7,153,314 B2 | 12/2006 | Laufer et al. |
| 7,248,944 B2 | 7/2007 | Green |
| 8,337,515 B2 | 12/2012 | Viola et al. |
| 8,628,545 B2 | 1/2014 | Cabrera et al. |
| 8,870,902 B2 * | 10/2014 | Deodhar ............ A61B 17/295 606/174 |
| 9,113,860 B2 | 8/2015 | Viola et al. |
| 9,237,900 B2 * | 1/2016 | Boudreaux ............ A61B 18/00 |
| 9,271,723 B2 | 3/2016 | Taylor et al. |
| 9,907,550 B2 | 3/2018 | Sniffin et al. |
| 2004/0010245 A1 | 1/2004 | Cerier et al. |
| 2004/0060410 A1 | 4/2004 | Leung et al. |
| 2005/0256533 A1 | 11/2005 | Roth et al. |
| 2006/0111732 A1 | 5/2006 | Gibbens et al. |
| 2006/0161185 A1 * | 7/2006 | Saadat ............ A61B 17/0487 606/153 |
| 2006/0184198 A1 * | 8/2006 | Bales ............ A61B 10/06 606/205 |
| 2006/0253126 A1 | 11/2006 | Bjerken et al. |
| 2006/0282093 A1 | 12/2006 | Shelton, IV et al. |
| 2007/0005110 A1 | 1/2007 | Collier et al. |
| 2008/0234725 A1 * | 9/2008 | Griffiths ............ A61B 17/29 606/208 |
| 2009/0259233 A1 | 10/2009 | Bogart et al. |
| 2012/0095298 A1 * | 4/2012 | Stefanchik ......... A61B 17/2909 600/219 |
| 2012/0104072 A1 | 5/2012 | Vidal et al. |
| 2012/0116416 A1 | 5/2012 | Neff et al. |
| 2012/0203270 A1 * | 8/2012 | Chen ............ A61B 17/29 606/205 |
| 2013/0085494 A1 * | 4/2013 | Weisenburgh, II ............ A61B 17/0469 606/41 |
| 2013/0197516 A1 * | 8/2013 | Kappel ............ A61B 17/295 606/46 |
| 2015/0150573 A1 * | 6/2015 | Van Tol ............ A61B 18/1447 606/34 |
| 2016/0303745 A1 * | 10/2016 | Rockrohr ............ A61B 34/71 |
| 2017/0348043 A1 * | 12/2017 | Wang ............ A61B 18/1445 |
| 2019/0388085 A1 * | 12/2019 | Nicholas ............ A61B 17/0625 |

FOREIGN PATENT DOCUMENTS

| | | |
|---|---|---|
| WO | 9811829 A1 | 3/1998 |
| WO | 0174254 A1 | 10/2001 |
| WO | 03017850 A2 | 3/2003 |
| WO | 03028541 A2 | 4/2003 |
| WO | 2006061868 A1 | 6/2006 |
| WO | 2009132284 A2 | 10/2009 |
| WO | 2016025132 A1 | 2/2016 |

* cited by examiner

SURGICAL SUTURING AND GRASPING DEVICE

CROSS-REFERENCE TO RELATED APPLICATION

This application claims the benefit of and priority to U.S. Provisional Patent Application No. 62/581,160 filed Nov. 3, 2017, the entire disclosure of which is incorporated by reference herein.

TECHNICAL FIELD

The present disclosure relates to surgical suturing, and more particularly, to devices, systems and methods for suturing and grasping tissue.

BACKGROUND

During laparoscopic suturing, a surgeon typically utilizes a needle driver with one hand and a tissue grasper with another hand. In many instances, the needle driver is used to hold the needle while passing it through tissue; and then used to grasp tissue as the tissue grasper is repositioned from grasping tissue to grasping the needle. To limit the need for instrument exchange, surgeons often utilize a needle driver to both grasp tissue and drive a needle or they use a tissue grasper to both drive a needle and grasp tissue. Unfortunately, a needle driver may not provide for a satisfactory tissue grasper and a tissue grasper may not provide for a satisfactory needle driver.

SUMMARY

The present disclosure is generally directed to a suturing and grasping device configured to provide the dual function of needle driving and tissue grasping. The suturing and grasping device includes a stationary jaw member and two movable jaw members. A first movable jaw member is configured to move relative to, and cooperate with, the stationary jaw member to grasp or retain tissue. A second movable jaw member is configured to move relative to, and cooperate with, the stationary jaw member to drive a needle for effectuating a suturing procedure.

In accordance with one aspect of the present disclosure, an endoscopic suturing and grasping device includes a handle assembly, a shaft assembly, and an end effector. The handle assembly includes a movable handle and a stationary handle. The shaft assembly extends from the handle assembly. The end effector is supported on the shaft assembly and includes a suturing jaw member, a stationary jaw member, and a grasping jaw member. The suturing jaw member is selectively movable relative to the stationary jaw member to drive a suturing needle between the suturing jaw member and the stationary jaw member. The grasping jaw member is selectively movable relative to the stationary jaw member to grasp tissue between the stationary jaw member and the grasping jaw member.

In some embodiments, the stationary jaw member may include a first plurality of grasping teeth and the grasping jaw member may include a second plurality of grasping teeth. The first and second pluralities of teeth may be configured to cooperate with one another as the grasping jaw member moves relative to the stationary jaw member. The stationary jaw member may include a first plurality of needle-driving teeth and the suturing jaw member may include a second plurality of needle-driving teeth. The first and second pluralities of needle-driving teeth may be configured to cooperate with one another as the suturing jaw member moves relative to the stationary jaw member.

In certain embodiments, the grasping jaw member and the suturing jaw member may be movable relative to the stationary jaw member independent of one another.

In embodiments, the movable handle of the handle assembly may be movable relative to the stationary handle member to selectively move at least one of the suturing jaw member or the grasping jaw member relative to the stationary jaw member. The movable handle may be movable in a first direction relative to the stationary handle to move the suturing jaw member relative to the stationary jaw member. The movable handle may be movable in a second direction relative to the stationary handle to move the grasping jaw member relative to the stationary jaw member. The first and second directions may be different.

In certain embodiments, the grasping jaw member may include a first cam plate that extends proximally therefrom and the suturing jaw member may include a second cam plate that extends proximally therefrom, the first and second cam plates coupled to a drive bar that is movable relative to the first and second cam plates to move one or both of the grasping jaw member or the suturing jaw member relative to the stationary jaw member. The drive bar may be coupled to the handle assembly and axially movable relative to the shaft assembly in response to movement of the movable handle. The first cam plate may define a first cam slot and the second cam plate may define a second cam slot. The drive bar may include a drive pin that translates along the first and second cam slots to move one or both of the grasping jaw member or the suturing jaw member relative to the stationary jaw member.

In some embodiments, the grasping jaw member and the suturing jaw member may be pivotably coupled to the stationary jaw member by a pin.

According to yet another aspect of the present disclosure, an end effector for a suturing and grasping device includes a stationary jaw member, a suturing jaw member, and a grasping jaw member. The suturing jaw member is selectively movable relative to the stationary jaw member to drive a suturing needle between the suturing jaw member and the stationary jaw member. The grasping jaw member is selectively movable relative to the stationary jaw member to grasp tissue between the stationary jaw member and the grasping jaw member.

In some embodiments, the grasping jaw member may include a first cam plate that extends proximally therefrom and the suturing jaw member may include a second cam plate that extends proximally therefrom. The first and second cam plates may be configured to couple to a drive bar that is movable relative to the first and second cam plates to move one or both of the grasping jaw member or the suturing jaw member relative to the stationary jaw member. The first cam plate may define a first cam slot and the second cam plate may define a second cam slot. The first and second cam slots may be configured to receive a drive pin that translates along the first and second cam slots to move one or both of the grasping jaw member or the suturing jaw member relative to the stationary jaw member. The first cam slot may include a first segment and a second segment. The first segment may be angled relative to the second segment in a first direction. The second cam slot may include a first segment and a second segment. The second segment of the second cam slot may be angled relative to the first segment of the second cam slot in a second direction that is different than the first direction.

In certain embodiments, the stationary jaw member may be disposed between the grasping jaw member and the suturing jaw member.

According to still another aspect of the present disclosure, a method of operating an end effector for a suturing and grasping device is provided. The method includes selectively moving a handle in a first direction to move a grasping jaw member of the end effector relative to a stationary jaw member of the end effector. The method further includes selectively moving the handle in a second direction to move a suturing jaw member of the end effector relative to the stationary jaw member of the end effector, the stationary jaw member disposed between the grasping jaw member and the stationary jaw member.

Advantageously, the presently disclosed suturing and grasping device provides jaws that can be operated independently to control multiple functions, such as needle driving for effectuating suturing and tissue grasping, to increase operating efficiency. Such structure also enables a clinician to choose any suitable suture and needle combination (e.g., different shapes/types of needles and/or sutures may be utilized). The presently disclosed suturing and grasping device may be provided as re-usable and/or reposable for limiting costs. Further still, the presently disclosed endoscopic suturing and grasping device also provides the benefit of enabling a clinician to efficiently suture while maintaining a field of view through a camera port. Further, the present disclosure provides the advantage of eliminating a need for instrument exchange between different suturing and tissue grasping devices during a procedure (e.g., a hernia defect closure) while maintaining tissue grasping and suturing proficiencies. Further, although described herein as an endoscopic/laparoscopic device, the presently disclosed suturing and grasping device may be provided as an open device.

BRIEF DESCRIPTION OF THE DRAWINGS

The accompanying drawings, which are incorporated in and constitute a part of this specification, illustrate embodiments of the present suturing and grasping devices and, together with a general description of the disclosure given above, and the detailed description of the embodiment(s) given below, serve to explain the principles of the disclosure, wherein.

DETAILED DESCRIPTION

Figure 1:
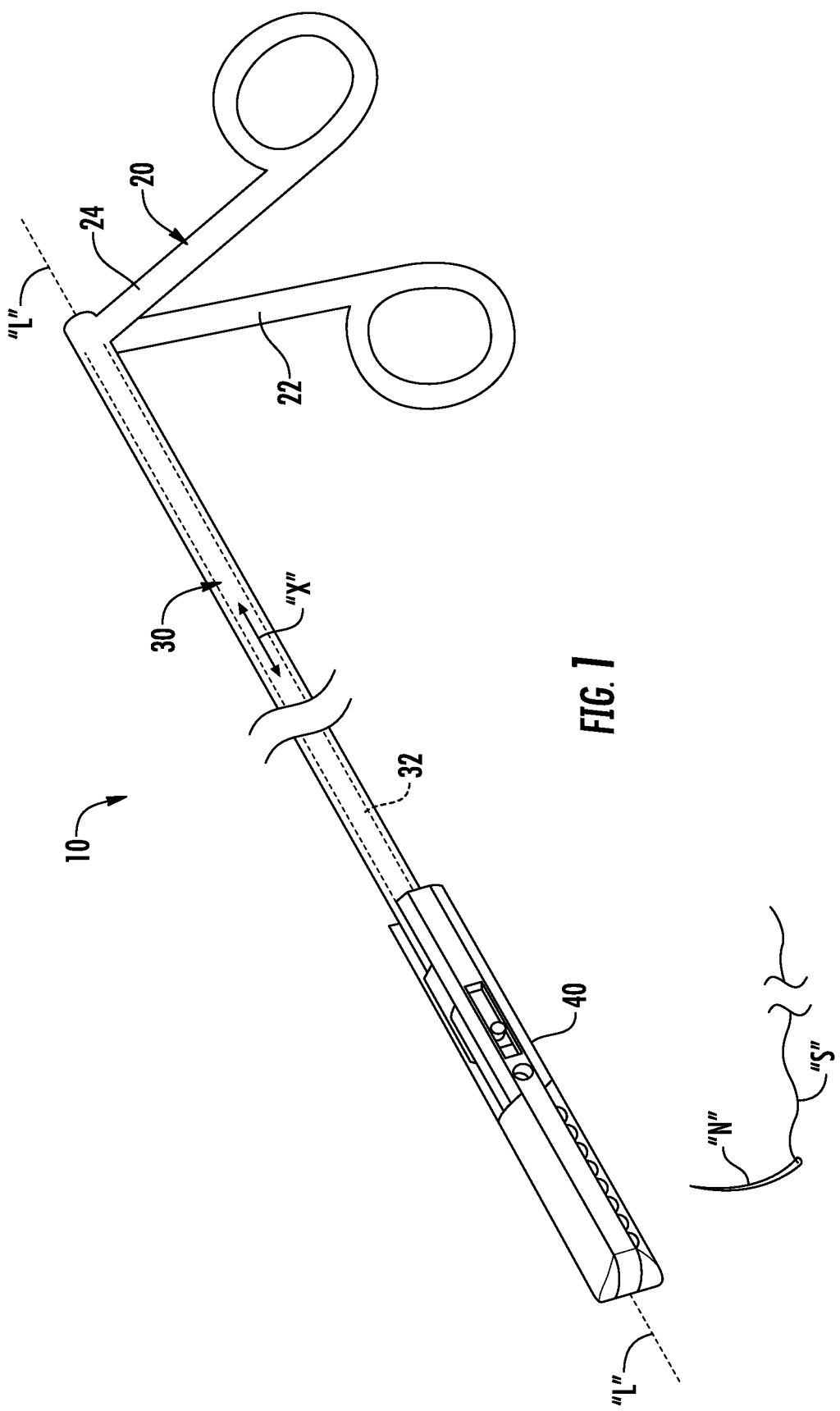
FIG. 1 is a perspective view of a suturing and grasping device, and a needle and suture used therewith in accordance an illustrative embodiment of the present disclosure.

Embodiments of the presently disclosed suturing and grasping devices are described in detail with reference to the drawings, in which like reference numerals designate identical or corresponding elements in each of the several views. As used herein, the term "distal" refers to that portion of structure farther from the user, while the term "proximal" refers to that portion of structure closer to the user. As used herein, the term "clinician" refers to a doctor, nurse, or other care provider and may include support personnel. Further, terms used herein such as "top," "bottom," "side" and similar directional terms are used simply for convenience of description and are not intended to limit the disclosure.

In the following description, well-known functions or constructions are not described in detail to avoid obscuring the present disclosure in unnecessary detail.

Referring now to FIG. 1, a suturing and grasping device, shown generally at 10, can be configured for endoscopic (e.g., laparoscopic) and/or open surgical procedures. Suturing and grasping device 10 includes a handle assembly 20, a shaft assembly 30 that extends distally from handle assembly 20, and an end effector 40 supported on a distal end portion of shaft assembly 30.

Figure 2:
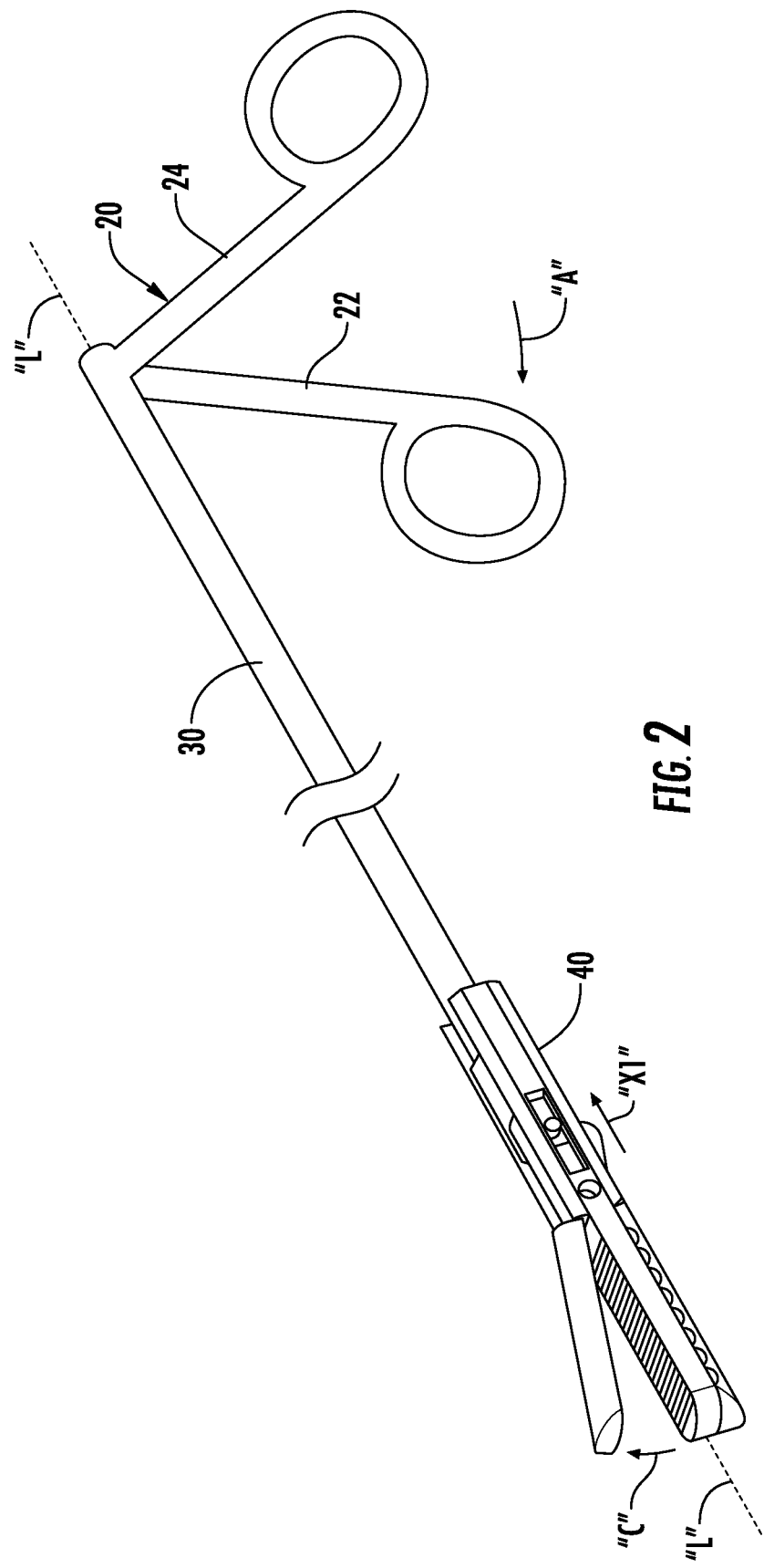
FIG. 2 is a perspective view of the suturing and grasping device illustrating an end effector thereof in a first position.
Figure 3:
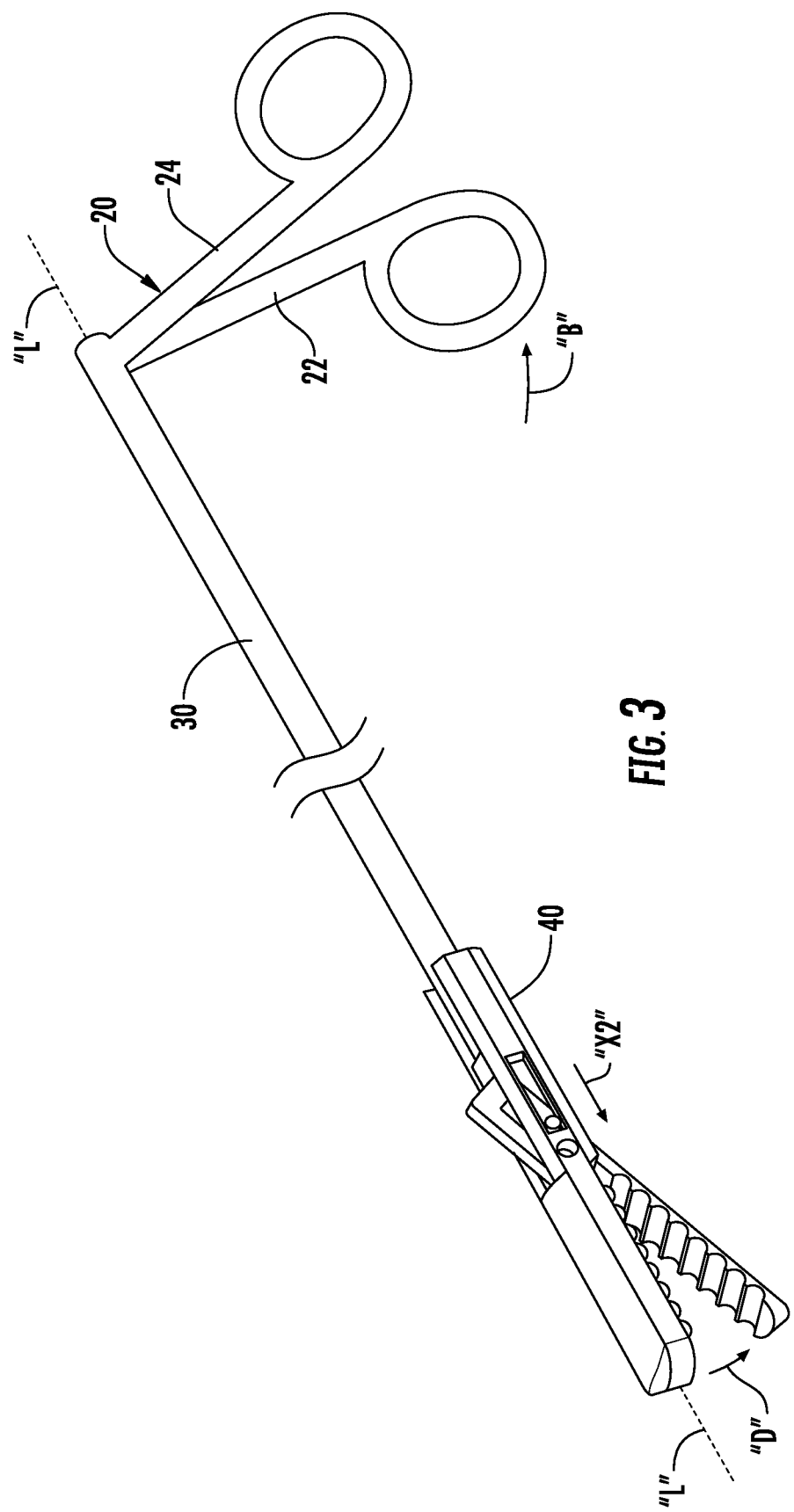
FIG. 3 a perspective view of the suturing and grasping device illustrating the end effector in a second position.

With reference now to FIGS. 1-3, handle assembly 20 of suturing and grasping device 10 includes a movable handle 22 and a stationary handle 24, and/or other suitable actuating mechanism (e.g., a robot, etc.). Movable handle 22 is pivotably coupled to handle assembly 20 (e.g., by a pin—not shown) and operably associated with drive assembly 32 of shaft assembly 30 to operate end effector 40 of suturing and grasping device 10. Movable handle 22 of handle assembly 20 is positioned to pivot relative to stationary handle 24. For example, as seen in FIGS. 2 and 3, movable handle 22 is positioned to move in a first direction (e.g., distally) relative to stationary handle 24, as indicated by arrow "A," and positioned to move in a second direction (e.g., proximally) relative to stationary handle 24, as indicated by arrow "B."

Figure 5:
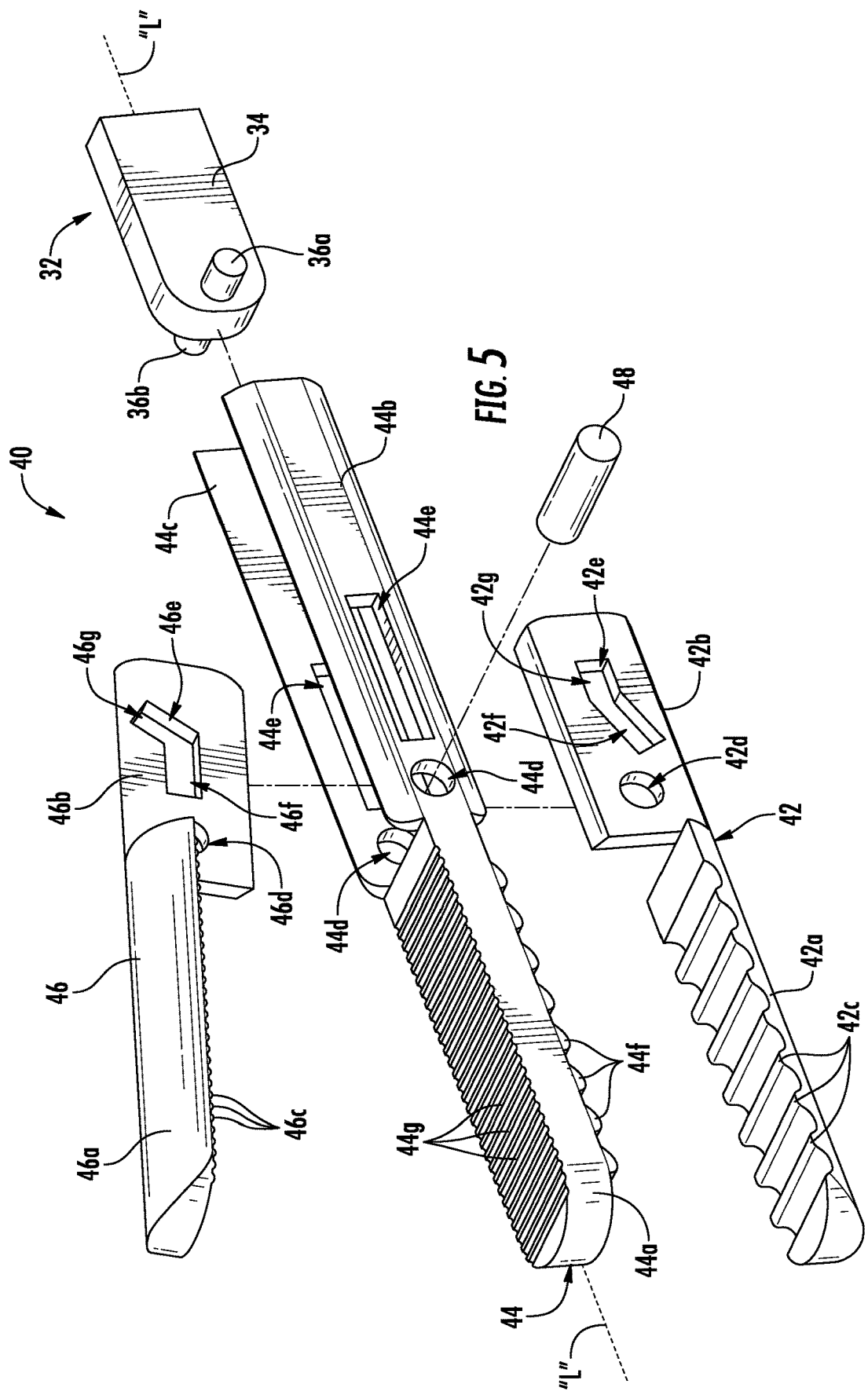
FIG. 5 is a perspective view, with parts separated, of the end effector.
Figure 6A:
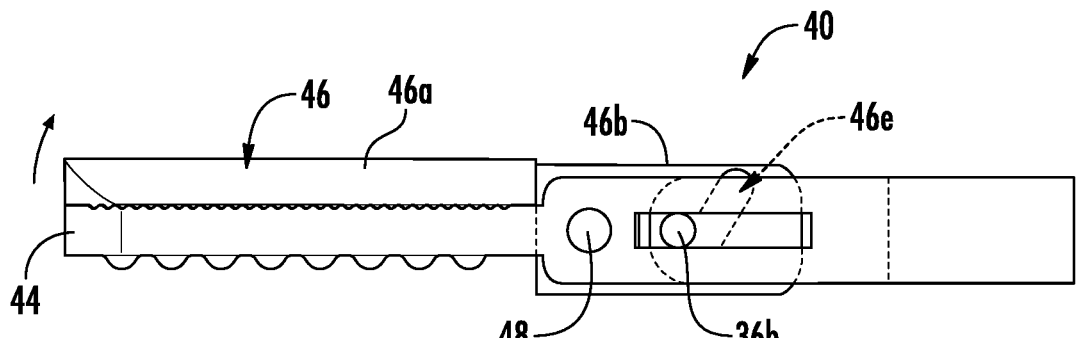
FIGS. 6A-6C are progressive, side views of the end effector illustrating movement of a grasping jaw member thereof relative to a stationary jaw member thereof, and with a suturing jaw thereof removed for clarity.
Figure 6B:
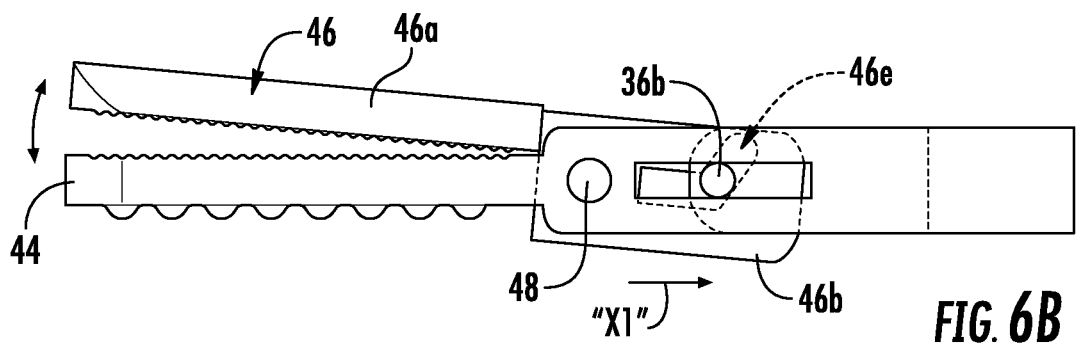
Figure 6C:
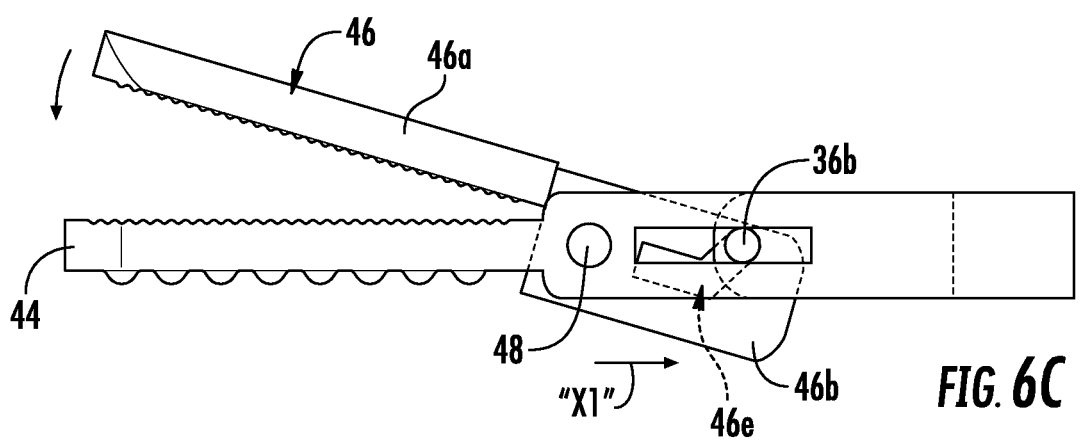
Figure 7A:
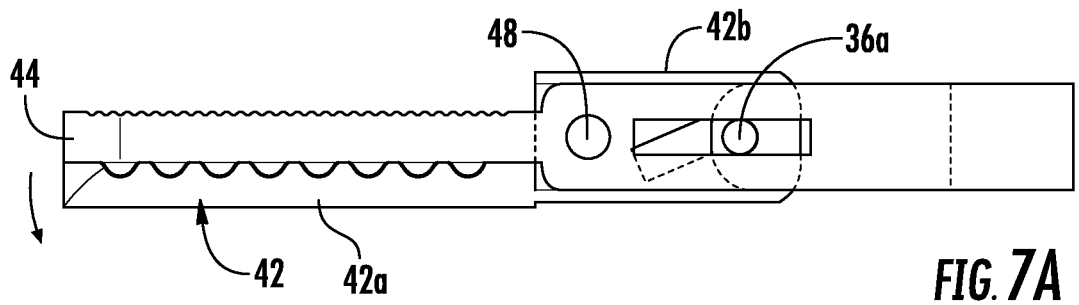
FIGS. 7A-7C are progressive, side views of the end effector illustrating movement of the suturing jaw thereof relative to the stationary jaw member thereof, and with the grasping jaw thereof removed for clarity.
Figure 7B:
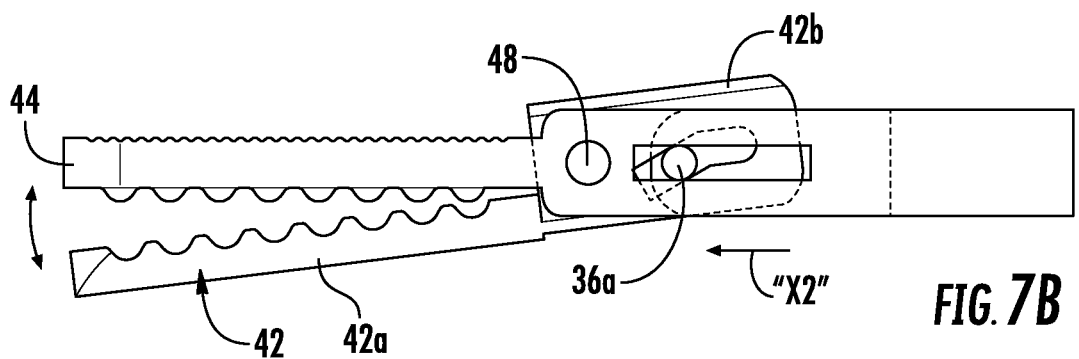
Figure 7C:
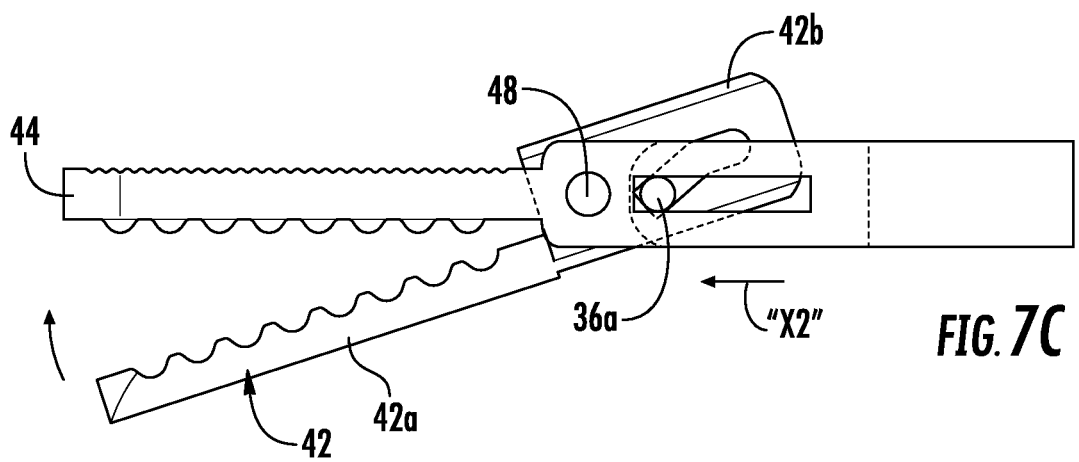
Figure 8A:
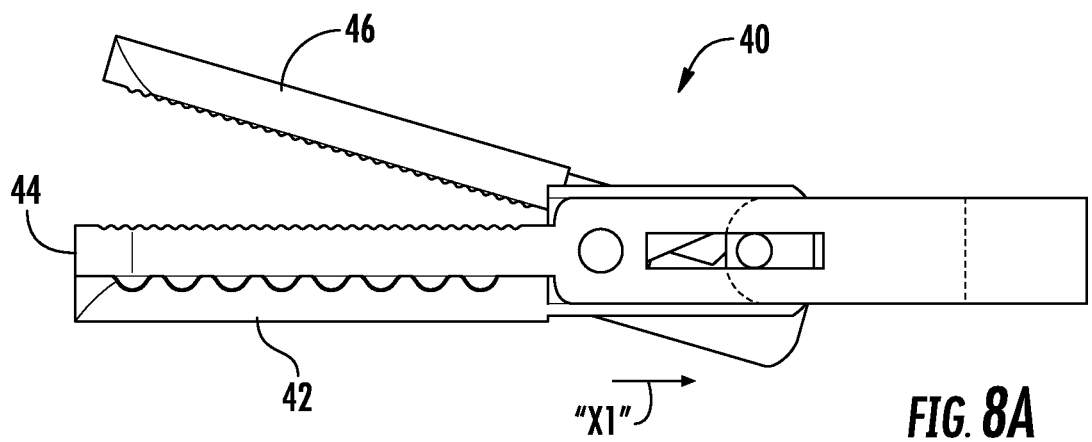
FIGS. 8A and 8B are progressive, side views of the end effector illustrating movement of the grasping and suturing jaw members relative to the stationary jaw member.
Figure 8B:
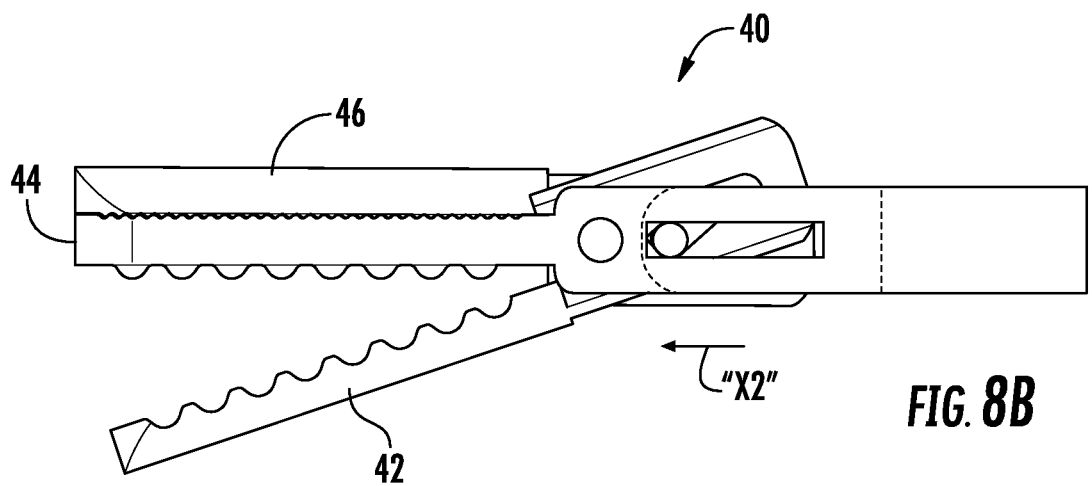

Referring to FIGS. 1 and 5, shaft assembly 30 of suturing and grasping device 10 defines a longitudinal axis "L-L" and supports a drive assembly 32. Drive assembly 32 is operably associated with handle assembly 20 at a proximal end portion thereof, and with end effector 40 at a distal end portion thereof. As seen in FIG. 5, drive assembly 32 includes a drive shaft 34 that has a proximal end portion that is operatively coupled to movable handle 22 of handle assembly 20, and a distal end portion that has first and second pins 36a, 36b extending laterally therefrom.

For a more detailed description of suitable surgical suturing devices, systems, and methods that can be modified to provide the suturing and grasping devices described herein, reference can be made, for example, to U.S. Pat. No. 8,337,515 and to U.S. Pat. No. 9,113,860, the entire contents of each of which are incorporated herein by reference.

Figure 4:
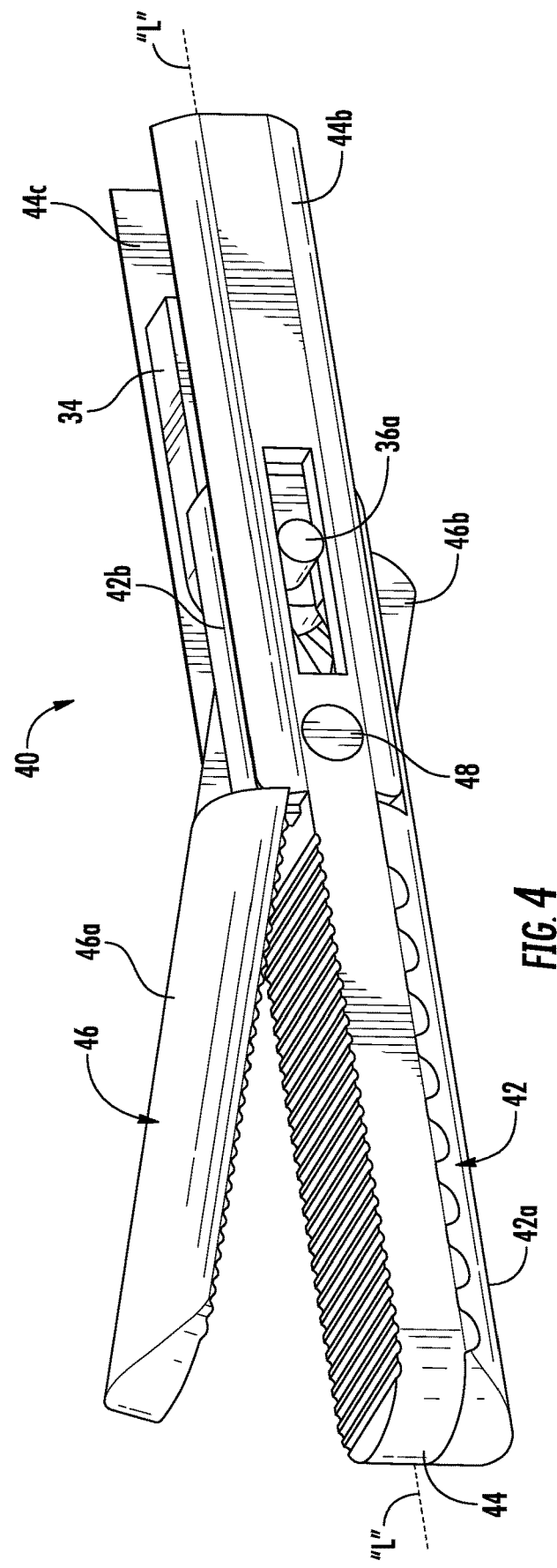
FIG. 4 is an enlarged, perspective view of the end effector in the first position.

Turning now to FIGS. 4 and 5, end effector 40 of suturing and grasping device 10 is supported on shaft assembly 30 (FIG. 1) of suturing and grasping device 10 and includes a suturing jaw member 42, a stationary jaw member 44, and a grasping jaw member 46. Suturing jaw member 42 and grasping jaw member 46 of end effector 40 are pivotably coupled to stationary jaw member 44 of end effector 40 by a pin 48 such that each of suturing jaw member 42 and grasping jaw member 46 are configured to independently pivot relative to stationary jaw member 44, as indicated by arrows "C" and "D" seen in FIGS. 2 and 3, respectively.

Suturing jaw member 42 of end effector 40 is positioned to pivot relative to the stationary jaw member 44 of end effector 40 to drive a suturing needle "N" (FIG. 1), grasped between suturing jaw member 42 and stationary jaw member 44, for passing suture "S" attached to suturing needle "N" back-and-forth through tissue (e.g., stitching tissue). Suture "S" can be secured to suturing needle "N" using any conventional method. For example, the suture "S" can be secured to suturing needle "N" by tying and/or knotting (e.g., by looping around an outer surface of the respective needle, by a coupling connector, etc.). Alternatively, and or additionally, suturing needle "N" can define any number of apertures (not shown) into and/or through which suture "S" may be secured.

Suturing jaw member 42 of end effector 40 includes a needle-driving jaw portion 42a, and a cam plate 42b that extends proximally from needle-driving portion 42a. Needle-driving portion 42a of suturing jaw member 42 includes a plurality of needle-driving teeth 42c that are transversely extending and axially spaced-apart, for example, longitudinally, along needle-driving portion 42a.

Cam plate 42b of suturing jaw member 42 defines a pin opening 42d therethrough at a distal portion of cam plate 42b, and a cam slot 42e that extends along a proximal portion of cam plate 42b. Cam slot 42e of cam plate 42b includes a first segment 42f and a second segment 42g, and is positioned to slidably receive first pin 36a of drive shaft 34 therealong. First segment 42f of cam slot 42e is angled relative to second segment 42g of cam slot 42e and relative to the longitudinal axis "L-L" of shaft assembly 30 of suturing and grasping device 10 when both suturing jaw member 44 and grasping jaw member 46 of end effector 40 are in a closed or approximated position (see FIG. 1) relative to stationary jaw member 44 of end effector 40. In the same position, second segment 42g of cam slot 42e of suturing jaw member 42 is disposed in mirrored relation to the longitudinal axis "L-L" of shaft assembly 30, or extends in a substantially parallel direction relative to the longitudinal axis "L-L".

Stationary jaw member 44 of end effector 40 includes a jaw portion 44a and first and second support plates 44b, 44c that extend from a proximal portion of jaw portion 44a. First and second support plates 44b, 44c of stationary jaw member 44 are laterally spaced-apart and positioned on opposite sides of jaw portion 44a to receive cam plates 42b, 46b of suturing jaw member 42 and grasping jaw member 46, respectively, between first and second support plates 44b, 44c. First and second support plates 44b, 44c are identical and each defines a pin opening 44d and an elongated channel 44e therethrough. Pin opening 44d is positioned to support pin 48 therein, and elongated channels 44e of first and second support plates 44b, 44c are positioned to slidably receive first and second pins 36a, 36b of drive shaft 34, respectively, therealong.

Jaw portion 44a of stationary jaw member 44 includes a plurality of needle-driving teeth 44f that are transversely extending and axially spaced-apart, for example, longitudinally, along a first surface (e.g., a bottom surface) of jaw portion 44a. Needle-driving teeth 44f of stationary jaw member 44 are positioned to selectively interdigitate with the plurality of needle-driving teeth 42c of suturing jaw member 42 of end effector 40 as suturing jaw member 42 pivots relative to stationary jaw member 44 of end effector 40. Jaw portion 44a of stationary jaw member 44 further includes a plurality of grasping teeth 44g that are transversely extending and axially spaced-apart, for example, longitudinally, along a second surface (e.g., a top surface) of jaw portion 44a. Grasping teeth 44g of stationary jaw member 44 are positioned to selectively interdigitate with a plurality of grasping teeth 46c of grasping jaw member 46 as grasping jaw member 46 pivots relative to stationary jaw member 44.

Grasping jaw member 46 of end effector 40 is positioned to pivot relative to stationary jaw member 44 of end effector 40 to grasp tissue (not shown) between stationary jaw member 44 and grasping jaw member 46. Grasping jaw member 46 includes a grasping jaw portion 46a and cam plate 46b that extends proximally from grasping jaw portion 46a. Grasping jaw portion 46a of grasping jaw member 46 includes grasping teeth 46c that are transversely extending and axially spaced-apart, for example, longitudinally, along grasping jaw portion 46a.

Grasping teeth 46c of grasping jaw member 46 are greater in number than needle-driving teeth 42c of suturing jaw member 42. While transversely extending teeth are shown and described for suturing jaw member 42, stationary jaw member 44, and grasping jaw member 46, it is envisioned and contemplated that teeth or grasping features for jaws 42, 44 and 46 may take any form or configuration.

Cam plate 46b of grasping jaw member 46 defines a pin opening 46d therethrough at a distal portion of cam plate 46b, and a cam slot 46e that extends longitudinally along a proximal portion of cam plate 46b. Cam slot 46e includes first and second segments 46f, 46g, and is positioned to slidably receive second pin 36b of drive shaft 34 therealong. Second segment 42g of cam slot 46e is angled relative to first segment 46f of cam slot 46e and relative to the longitudinal axis "L-L" of shaft assembly 30 of suturing and grasping device 10 when both suturing jaw member 44 and grasping jaw member 46 of end effector 40 are in a closed or approximated position (see FIG. 1) relative to stationary jaw member 44 of end effector 40. In the same position, first segment 46f of cam slot 46e of grasping jaw member 46 is disposed in mirrored relation to the longitudinal axis "L-L" of shaft assembly 30, or extends in a substantially parallel direction relative to the longitudinal axis "L-L". In this regard, cam slot 42e of suturing jaw member 42 and cam slot 46e of grasping jaw member 46 are disposed in reverse or opposite orientations along the longitudinal axis "L-L" of shaft assembly 30 to enable suturing jaw member 42 and grasping jaw member 46 to separately pivot relative to stationary jaw member 44.

In use, as illustrated in FIGS. 2, 3, 5, 6A-6C, 7A-7C, and 8A and 8B, movable handle 22 of handle assembly 20 of suturing and grasping device 10 is pivotable relative to stationary handle 24 of handle assembly 20 to axially translate drive shaft 34 of drive assembly 32 of suturing and grasping device 10, as indicated by arrows "X" in FIG. 1. As drive shaft 34 of drive assembly 32 translates from a neutral position (e.g., with pins 36a, 36b of drive shaft 34 centrally disposed along elongated channels 44e of stationary jaw member 44, see FIGS. 1 and 6A) toward a proximal direction, as indicated by arrow "X1" illustrated in FIGS. 2, 6B, and 6C, for example, grasping jaw member 46 pivots from a closed or approximated position (FIG. 6A) relative to stationary jaw member 44 toward an open or unapproximated position (FIG. 6C) relative to stationary jaw member 44. As drive shaft 34 translates back toward the neutral position (FIG. 1), grasping jaw member 46 pivots toward the closed or approximated position relative to the stationary jaw member 44. As grasping jaw member 46 pivots relative to stationary jaw member 44, for example, to grasp tissue between grasping teeth 46c, 46g of respective grasping and stationary jaw members 46, 44, suturing jaw member 42 remains in a closed or approximated position relative to stationary jaw member 44.

In similar fashion, as drive shaft 34 of drive assembly 32 translates from the neutral position (see FIGS. 1 and 7A) toward a distal direction, as indicated by arrow "X2" (see FIGS. 3, 7B, 7C, 8B), suturing jaw member 42 pivots from a closed or approximated position (FIG. 7A) relative to stationary jaw member 44 toward an open or unapproximated position (FIG. 7C) relative to stationary jaw member 44. Likewise, as drive shaft 34 translates back toward the neutral position (FIG. 1), suturing jaw member 42 pivots back toward the closed or approximated position thereof. As suturing jaw member 42 pivots relative to stationary jaw member 44, for example, to drive needle "N" back-and-forth between needle-driving teeth 42c, 44f of suturing jaw member 42 and stationary jaw member 44, respectively, for passing suture "S" through tissue, grasping jaw member 46 remains in its closed position relative to stationary jaw member 44.

In some embodiments, end effector 40 may include one or more locking features such as surface texturing, detents, springs, ratchet and pawl, etc., or combinations thereof, which function to lock or bias one of suturing jaw member 42 or grasping jaw member 46 in its respective closed position relative to stationary jaw member 44 while the other pivots relative to stationary jaw member 44.

Any of the components of the presently described devices can be formed of any suitable metallic and/or polymeric material. Securement of any of the components of the presently described devices to any of the other components of the presently described devices can be effectuated using known fastening techniques such welding (e.g., ultrasonic), crimping, gluing, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An endoscopic suturing and grasping device comprising:
   a handle assembly including a movable handle and a stationary handle;
   a shaft assembly extending from the handle assembly; a suturing needle and
   an end effector supported on the shaft assembly and including a suturing jaw member, a stationary jaw member, and a grasping jaw member the suturing jaw member positioned on a first side of the stationary jaw member, the grasping jaw member positioned on a second side of the stationary jaw member, wherein the first side is opposite the second side, the suturing jaw member selectively movable relative to the stationary jaw member to drive the suturing needle between the suturing jaw member and the stationary jaw member, the grasping jaw member selectively movable relative to the stationary jaw member to grasp tissue between the stationary jaw member and the grasping jaw member; wherein the stationary jaw member includes a first plurality of grasping teeth and the grasping jaw member includes a second plurality of grasping teeth, the first and second pluralities of teeth configured to cooperate with one another as the grasping jaw member moves relative to the stationary jaw member; the stationary jaw member includes a first plurality of needle-driving teeth and the suturing jaw member includes a second plurality of needle-driving teeth, the first and second pluralities of needle-driving teeth configured to cooperate with one another as the suturing jaw member moves relative to the stationary jaw member.

2. The endoscopic suturing and grasping device of claim 1, wherein the grasping jaw member and the suturing jaw member are movable relative to the stationary jaw member independent of one another.

3. The endoscopic suturing and grasping device of claim 1, wherein the movable handle of the handle assembly is movable relative to the stationary handle member to selectively move at least one of the suturing jaw member or the grasping jaw member relative to the stationary jaw member.

4. The endoscopic suturing and grasping device of claim 3, wherein the movable handle is movable in a first direction relative to the stationary handle to move the suturing jaw member relative to the stationary jaw member, and the movable handle is movable in a second direction relative to the stationary handle to move the grasping jaw member relative to the stationary jaw member, the first and second directions being different.

5. The endoscopic suturing and grasping device of claim 1, wherein the grasping jaw member includes a first cam plate that extends proximally therefrom and the suturing jaw member includes a second cam plate that extends proximally therefrom, the first and second cam plates coupled to a drive bar that is movable relative to the first and second cam plates to move at least one of the grasping jaw member or the suturing jaw member relative to the stationary jaw member.

6. The endoscopic suturing and grasping device of claim 5, wherein the drive bar is coupled to the handle assembly and axially movable relative to the shaft assembly in response to movement of the movable handle.

7. The endoscopic suturing and grasping device of claim 5, wherein the first cam plate defines a first cam slot and the second cam plate defines a second cam slot, and wherein the drive bar includes a drive pin that translates along the first and second cam slots to move at least one of the grasping jaw member or the suturing jaw member relative to the stationary jaw member.

8. The endoscopic suturing and grasping device of claim 1, wherein the grasping jaw member and the suturing jaw member are pivotably coupled to the stationary jaw member by a pin.

\* \* \* \* \*